United States Patent
Champagne et al.

(10) Patent No.: US 11,414,604 B2
(45) Date of Patent: Aug. 16, 2022

(54) SUBMICRONIC EMULSION

(71) Applicant: COATEX, Genay (FR)

(72) Inventors: Clementine Champagne, Caluire-et-Cuire (FR); Jean-Marc Suau, Lucenay (FR)

(73) Assignee: COATEX, Genay (FR)

(*) Notice: Subject to any disclaimer, the term of this patent is extended or adjusted under 35 U.S.C. 154(b) by 135 days.

(21) Appl. No.: 16/759,940

(22) PCT Filed: Dec. 21, 2018

(86) PCT No.: PCT/FR2018/053516
§ 371 (c)(1),
(2) Date: Apr. 28, 2020

(87) PCT Pub. No.: WO2019/122784
PCT Pub. Date: Jun. 27, 2019

(65) Prior Publication Data
US 2021/0178350 A1    Jun. 17, 2021

(30) Foreign Application Priority Data

Dec. 21, 2017   (FR) ..................................... 1762696

(51) Int. Cl.
C08F 220/06 (2006.01)
C09K 23/00 (2022.01)
C08F 220/18 (2006.01)
C09D 5/02 (2006.01)
C09D 167/08 (2006.01)
B01F 23/41 (2022.01)

(52) U.S. Cl.
CPC .......... *C09K 23/00* (2022.01); *B01F 23/4105* (2022.01); *C08F 220/06* (2013.01); *C08F 220/1802* (2020.02); *C09D 5/022* (2013.01); *C09D 5/024* (2013.01); *C09D 167/08* (2013.01); *B01F 2215/0495* (2013.01)

(58) Field of Classification Search
CPC .......... B01F 17/0028; B01F 2215/0495; B01F 3/0811; C08F 220/06; C08F 220/1802; C09D 5/024; C09D 167/08; C09D 5/022
USPC ......................................................... 524/501
See application file for complete search history.

(56) References Cited

U.S. PATENT DOCUMENTS

| | | |
|---|---|---|
| 2002/0035182 A1 | 3/2002 | L'Alloret et al. |
| 2006/0030655 A1 | 2/2006 | L'Alloret et al. |
| 2007/0036831 A1 | 2/2007 | Baker |
| 2011/0200657 A1 | 8/2011 | Baker |
| 2018/0177723 A1* | 6/2018 | Devraj ................. A61K 47/183 |

FOREIGN PATENT DOCUMENTS

| | | |
|---|---|---|
| EP | 1 172 077 A1 | 1/2002 |
| WO | WO 2008/087211 A1 | 7/2008 |
| WO | WO 2015/155703 A2 | 10/2015 |
| WO | WO 2017/182265 A1 | 10/2017 |

OTHER PUBLICATIONS

International Search Report dated Apr. 15, 2019 in PCT/FR2018/053516 filed Dec. 21, 2018, 2 pages.

* cited by examiner

*Primary Examiner* — Hui H Chin
(74) *Attorney, Agent, or Firm* — Oblon, McClelland, Maier & Neustadt, L.L.P.

(57) ABSTRACT

The invention relates to a process for preparing a dispersion of a lipophilic compound in a continuous hydrophilic phase, the morphology of which is submicronic. During the preparation of this dispersion, there is applied, by means of a device which produces a shearing gradient less than 5000 $s^{-1}$, a shear stress from 100 to 5000 Pa during the addition of the lipophilic compound in the continuous phase which comprises a rheology-modifying compound selected from anionic copolymers, preferably an anionic polymer, in particular an ASE polymer or a HASE polymer. The dispersed particles of the lipophilic compound are nanometric particles whose size is less than 1 μm. The dispersion, particularly in the form of an emulsion, can be used in numerous fields.

17 Claims, No Drawings

SUBMICRONIC EMULSION

The invention relates to a method of preparing a dispersion of lipophilic compound in a continuous hydrophilic phase, the morphology of which is submicronic. When preparing this dispersion, a shear stress ranging from 100 to 5,000 Pa is applied, using a device producing a shear gradient of less than 5,000 s$^{-1}$, when adding the lipophilic compound in the continuous phase which comprises a rheology-modifying compound chosen among the anionic copolymers, preferably an anionic polymer, particularly an ASE polymer or an HASE polymer. The dispersed particles of lipophilic compound are nanometric particles of less than 1 μm in size. The dispersion, particularly as an emulsion, can be used in many fields.

Many fields require the combination of substances with properties that make them incompatible. It is particularly important to be able to combine a lipophilic compound and a hydrophilic compound.

It is therefore essential to have methods for preparing a dispersion of a lipophilic compound in a hydrophilic phase.

In addition to being able to prepare such dispersions, in particular as emulsions, it is also essential to provide methods leading to stable dispersions.

Emulsification of two incompatible substances is a non-equilibrium method that consists of applying mechanical energy to break down macroscopic areas of the substance to be dispersed and stabilising the resulting dispersion.

Generally, dispersion preparation methods, particularly emulsion, use physical stress when mixing the two phases to be combined. Applying shear stress during this combination is a very common procedure. The shear stress value that is applied is an essential factor in controlling the size of the particles of lipophilic compound that are dispersed in the hydrophilic phase.

The hydrophilic phase is most often in a gelled form, in particular to facilitate the preparation of the dispersion or to improve the stability of this dispersion.

A major drawback encountered when preparing dispersions is the destabilisation, or even the breakdown, of the hydrophilic phase gel, particularly when this destabilisation or breakdown occurs when applying the shear stress.

When this happens, this destabilisation or breakdown makes it impossible to obtain sub-micrometric or nanometric particle sizes.

The resulting dispersions are not consistent with the intended purpose and are thus generally unusable.

Indeed, many technical areas require the use of dispersions in which the lipophilic compound is in the form of very small particles and particularly submicron-size particles. It is therefore essential to have methods for preparing a dispersion of lipophilic compound in the form of nanometric particles.

Moreover, it is also essential to be able to prepare dispersions using common mechanical devices, in particular widely-available mixers or blenders. In particular, it is especially advantageous to be able to prepare dispersions using mixers or blenders that produce a low shear gradient, for example under 5,000 s$^{-1}$, or under 2,000 s$^{-1}$ or less.

Likewise, it is essential to have dispersion preparation methods in which the continuous hydrophilic phase is stable, particularly in the form of a stable gel, and is not broken down or fractured when applying mechanical stress.

Preferably, dispersion preparation methods should make it possible to control the texture of the prepared dispersions.

Document WO 2015 155703 describes a nanodispersion comprising an aqueous dispersion medium, a dispersed phase, a surface-active agent and optionally an additive. This nanodispersion is self-emulsifying and does not comprise any anionic copolymers. Document EP 1951200 discloses a composition comprising a nanoemulsion that can be used for its anti-inflammatory activity. Document WO 2017 182265 discloses a nanoemulsion comprising a significant amount of surface-active compound which is an N-acyl amino monocarboxylic salt. Document EP 1172077 describes an oil-in-water nanoemulsion in which the oil droplets are comprised of a non-ionic or anionic amphiphilic lipid. It does not comprise any anionic copolymers.

The dispersion preparation methods of the prior art do not make it possible to prepare dispersions in a satisfactory or effective way.

The method according to the invention provides a solution to all or part of the dispersion preparation methods of the prior art.

Thus, the invention provides a method of preparing a dispersion (D) comprising:
  a continuous hydrophilic phase comprising at least one hydrophilic compound and at least one rheology-modifying compound of the hydrophilic compound, and chosen among the anionic copolymers and
  a lipophilic phase dispersed in the continuous phase in the form of nanometric particles,
comprising:
  the preparation of a mixture (M) comprising the hydrophilic compound and the rheology-modifying compound of the hydrophilic compound,
  the addition of the lipophilic compound in the continuous phase by applying, using a device producing a shear gradient of less than 5,000 s$^{-1}$, a stress chosen among a shear stress ranging from 100 to 5,000 Pa and an extensional stress ranging from 100 to 5,000 Pa.

Preferably, the dispersion (D) is an emulsion. More preferably, the dispersion is an emulsion of the dispersed lipophilic phase in the continuous hydrophilic phase.

Particularly advantageously, the method according to the invention makes it possible to prepare the dispersion (D) in the absence of any surface-active compound which is generally used to trigger the self-emulsion of the lipophilic phase to be dispersed.

The method according to the invention makes it easy to prepare a dispersion (D) in which the lipophilic phase is dispersed in the continuous hydrophilic phase in the form of nanometric particles. According to the invention, the lipophilic phase particles are thus less than 1 μm in size, thus strictly less than 1,000 nm. The method according to the invention therefore makes it possible to prepare a dispersion (D) for which the mean size (measured by light scattering) of the particles of dispersed lipophilic phase is submicronic.

Preferably, at least 30% in volume or at least 40% in volume, more preferentially at least 50% in volume, of the dispersed lipophilic phase particles have a mean size that is nanometric or submicronic.

More preferably, at least 30% in volume or at least 40% in volume, more preferentially at least 50% in volume, of the dispersed lipophilic phase particles have a mean size ranging from 50 to 999 nm or from 100 to 999 nm or from 50 to 990 nm or from 500 to 990 nm. The method according to the invention makes it possible to control the viscosity of the prepared continuous hydrophilic phase. According to the invention, viscosity is measured using a rheometer, for example using a Mars III rheometer (Thermofisher).

Preferably according to the invention, the continuous hydrophilic phase has a viscosity ranging from 20 to 50,000 mPa·s. More preferably according to the invention, the continuous hydrophilic phase has a viscosity ranging from 100 to 50,000 mPa·s or from 100 to 20,000 mPa·s.

The method according to the invention also makes it possible to control the viscosity of the prepared dispersion (D). Preferably according to the invention, the dispersion (D) has a viscosity ranging from 20 to 50,000 mPa·s. More preferably according to the invention, the dispersion (D) has a viscosity ranging from 100 to 50,000 mPa·s or from 100 to 20,000 mPa·s. According to the invention, the preparation of the dispersion (D) may comprise an additional step that makes it possible to increase its viscosity. Moreover, an additional pH reduction step can make it possible to lower the viscosity of the dispersion (D).

The method of preparation according to the invention allows for the use of a wide variety of lipophilic compounds. Preferably, the lipophilic compound used according to the invention is a lipophilic compound that is useful in a field chosen among cosmetics, paints, dyes, printing, inks, construction, fuels, lubricants, anti-foaming agents, metallurgy, fertilisers, pharmaceuticals, agro-chemicals, crop protection products, detergents, food, leather, coating, in particular textile coating.

More preferably according to the invention, the lipophilic compound is a compound that is non-miscible in water at room temperature or miscible in water at room temperature in an amount by weight of less than 0.1% by weight relative to the amount of water.

Particularly advantageously, the respective amounts of hydrophilic and lipophilic phases can vary quite widely in the dispersion (D). Preferably, the dispersion (D) comprises from 0.1 to 75% by weight or from 0.3 to 75% by weight or from 1 to 75% by weight, of dispersed lipophilic phase relative to the total amount by weight of continuous hydrophilic phase and of dispersed lipophilic phase.

Also preferably, the dispersion (D) comprises from 0.1 to 70% by weight or from 0.3 to 70% by weight or from 1 to 70% by weight, of dispersed lipophilic phase relative to the total amount by weight of continuous hydrophilic phase and of dispersed lipophilic phase. More preferentially, the dispersion (D) comprises from 0.1 to 65% by weight or from 0.3 to 65% by weight or from 1 to 65% by weight, of dispersed lipophilic phase relative to the total amount by weight of continuous hydrophilic phase and of dispersed lipophilic phase.

Also more preferentially, the dispersion (D) comprises from 0.1 to 60% by weight or from 0.3 to 60% by weight or from 1 to 60% by weight, of dispersed lipophilic phase relative to the total amount by weight of continuous hydrophilic phase and of dispersed lipophilic phase.

Preferably according to the invention, the hydrophilic compound is water. The hydrophilic compound can also be water in a mixture with at least one other compound. Preferably, this mixture comprises water and a compound chosen among glycerol, polyglycerols, glycols, for example propylene glycol, butylene glycol, moistening compounds, for example moistening compounds for cosmetic compositions, sugar derivatives, for example xylitol, maltitol, coalescing agents, for example polyalkylene glycols with low molecular mass, in particular polyethylene glycol, butyl diglycol.

According to the invention, the preferred moistening compounds are water-soluble or hydrophilic. Preferably, they are chosen among a synthetic water-soluble compound, a naturally-derived water-soluble compound and combinations thereof, particularly a plant-based water-soluble compound; for example a water-soluble compound (a) chosen among diols, triols, sugars, modified sugars, ethers, protein compounds, amino acids, triglycerides and combinations thereof, particularly a water-soluble compound (a) chosen among pidolic acid (PCA; CAS No. 98-79-3 L-form or S(−)-form; 4042-36-8 D-form or R(+)-form; 149-87-1 racemic form); PCA derivatives, particularly arginine PCA, chitosan PCA, copper PCA derivative, ethyl hexyl PCA, lauryl PCA, magnesium PCA derivative, sodium PCA derivative, zinc PCA derivative; butylene glycol, pentylene glycol; calcium gluconate; fructose; glucose; isomalt; lactose; maltitol; mannitol; polydextrose; sorbitol; saccharose; sucrose; xylitol; glycerol; glycerine; glycyrrhizic acid; glycyrrhizic acid derivatives; histidine; hyaluronic acid; hyaluronic acid salts, particularly sodium hyaluronate; silk hydrolysate; keratin hydrolysate; soy hydrolysate; PEG-7; PEG-8; PEG-10; PEG-12; PEG-14; phytantriol; propylene glycol; silk (*Serica*); urea; propylene glycol-1,2,6; hexanetriol; butylene glycol; capryl glycol; dipropylene glycol; erythritol; triethylene glycol; hexylene glycol; phytantriol hexanediol; beeswax triol; organic moisteners; panthenol; provitamin B5; inositol glycogen; sugars and modified polyglyceryl sugars; sorbitol, honey; polymer polyols; inositol; vitamin B7, high-intensity-sweetening liquorice saponin, ethers; isoceteth-x, isolaureth-x; laneth-x; laureth-x; steareth-x; polyethylene glycols; polyethylene glycol derivatives; trideceth-(5-50); tridecanol polyethylene glycol ether; silicone copolyols; protein-based moistening compounds; cocodimonium hydroxypropyl hydrolysed casein; cocodimonium hydroxypropyl hydrolysed collagen; cocodimonium hydroxypropyl hydrolysed keratin; cocodimonium hydroxypropyl hydrolysed rice proteins; cocodimonium hydroxypropyl hydrolysed silk proteins; cocodimonium hydroxypropyl hydrolysed soy proteins; cocodimonium hydroxypropyl hydrolysed wheat proteins; cocodimonium hydroxypropyl silk amino acids; cocoyl hydrolysed collagen; cocoyl hydrolysed keratin; keratin; hydrolysed keratin; hydrolysed wheat proteins; hydrolysed quinoa proteins; potassium cocoyl hydrolysed collagen; triethanolamine-cocoyl hydrolysed collagen; triethanolamine-cocoyl hydrolysed soy proteins; histidine; amino acids; triglycerides; glyceryl triacetate; glyceryl triacetate obtained by natural glycerine esterification; alpha-hydroxy acids; fructose derivatives; milk fructose derivatives; fruit acids; lactic acid; neoagarobiose; *Aloe vera*.

Essentially, the method according to the invention uses at least one rheology-modifying compound of the hydrophilic compound chosen among the anionic copolymers.

According to the invention, the consistency of the rheology-modifying compound in the mixture (M) also comprising the hydrophilic compound may vary quite widely, in particular to enable effective control of the viscosity of the mixture (M).

Preferably, the consistency by weight of rheology-modifying compound in the mixture (M) ranges from 4 to 14% by weight of mixture (M) and the viscosity of the mixture (M) ranges from 300 to 5,000 mPa·s.

Also preferably, the consistency by weight of rheology-modifying compound in the mixture (M) ranges from 4 to 12% by weight of mixture (M) and the viscosity of the mixture (M) ranges from 300 to 2,000 mPa·s.

Also preferably, the consistency by weight of rheology-modifying compound in the mixture (M) ranges from 4 to 11% by weight of mixture (M) and the viscosity of the mixture (M) ranges from 300 to 1,000 mPa·s.

Also preferably, the consistency by weight of rheology-modifying compound in the mixture (M) ranges from 2.5 to 12% by weight of mixture (M) and the viscosity of the mixture (M) ranges from 100 to 2,000 mPa·s.

Also preferably, the consistency by weight of rheology-modifying compound in the mixture (M) ranges from 2.5 to 11% by weight of mixture (M) and the viscosity of the mixture (M) ranges from 100 to 1,000 mPa·s.

According to the invention, the rheology-modifying compound generally has a pH of greater than 5, preferably greater than 5.5. More preferentially, the pH is greater than 6. According to the invention, the rheology-modifying compound is chosen among the ASE copolymers, the HASE copolymers and combinations thereof.

According to the invention, the preferred anionic copolymers are prepared by polymerisation reaction:
(a1) of at least one anionic monomer comprising at least one polymerisable olefinic unsaturation, preferably an anionic monomer comprising at least one polymerisable olefinic unsaturation and at least one carboxylic acid group, preferably the anionic monomer is chosen among acrylic acid, methacrylic acid, maleic acid, maleic anhydride, itaconic acid, crotonic acid, an acrylic acid salt, a methacrylic acid salt, a maleic acid salt, a maleic anhydride salt, an itaconic acid salt, a crotonic acid salt and combinations thereof, much more preferentially acrylic acid or methacrylic acid and
(a2) of at least one ester of a compound derived from an acid chosen among acrylic acid, methacrylic acid, maleic acid, maleic anhydride, itaconic acid and crotonic acid, preferably an acrylic acid ester or a methacrylic acid ester, preferably chosen among methyl acrylate, ethyl acrylate, propyl acrylate, butyl acrylate, ethyl hexyl acrylate, methyl methacrylate, ethyl methacrylate, propyl methacrylate, butyl methacrylate, ethyl hexyl methacrylate, and combinations thereof.

Also preferably, the anionic copolymers are prepared by a polymerisation reaction that also uses:
(a3) at least one compound of formula (I):

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents a group comprising at least one polymerisable olefinic unsaturation, preferably an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group.

Also preferably, the anionic copolymers are prepared by a polymerisation reaction that also uses:
(a4) at least one compound chosen among 2-acrylamido-2-methylpropane sulphonic acid, ethoxymethacrylate sulphonic acid, sodium methallyl sulphonate, styrene sulphonate, hydroxyethyl acrylate phosphate, hydroxypropyl acrylate phosphate, hydroxyethylhexyl acrylate phosphate, hydroxyethyl methacrylate phosphate, hydroxypropyl methacrylate phosphate, hydroxyethylhexyl methacrylate phosphate, their salts and combinations thereof.

Also preferably, the anionic copolymers are prepared by a polymerisation reaction that also uses:
(a5) at least one compound chosen among hydroxyethyl acrylate, hydroxypropyl acrylate, hydroxyethylhexyl acrylate, hydroxyethyl methacrylate, hydroxypropyl methacrylate, hydroxyethylhexyl methacrylate.

Also preferably, the anionic copolymers are prepared by a polymerisation reaction that also uses:
(a6) at least one cross-linking monomer or at least one monomer comprising at least two olefinic unsaturations.

The particularly preferred anionic copolymers according to the invention are prepared by a polymerisation reaction that uses:
(a1) acrylic acid, methacrylic acid or acrylic acid and methacrylic acid,
(a2) methyl acrylate, methyl methacrylate or methyl acrylate and methyl methacrylate,
(a3) of at least one compound of formula (I):

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group.

Other particularly preferred anionic copolymers according to the invention are prepared by a polymerisation reaction that also uses:
(a1) acrylic acid, methacrylic acid or acrylic acid and methacrylic acid,
(a2) methyl acrylate, methyl methacrylate or methyl acrylate and methyl methacrylate,
(a3) at least one compound of formula (I):

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group and
(a4) 2-acrylamido-2-methylpropane sulphonic acid.

Other particularly preferred anionic copolymers according to the invention are prepared by a polymerisation reaction that also uses:
- (a1) acrylic acid, methacrylic acid or acrylic acid and methacrylic acid,
- (a2) methyl acrylate, methyl methacrylate or methyl acrylate and methyl methacrylate,
- (a4) 2-acrylamido-2-methylpropane sulphonic acid.

When preparing the rheology-modifying compound used according to the invention, it is possible to use at least one chain transfer agent, preferably chosen among the mercaptan compounds, in particular mercaptan compounds comprising at least four carbon atoms such as butyl mercaptan, n-octyl mercaptan, n-dodecyl mercaptan, tert-dodecyl mercaptan.

Preferably according to the invention, the mixture (M) comprises from 0.5 to 15% by weight, preferably from 1 to 15% by weight or from 2 to 12% by weight, of rheology modifier. More preferably according to the invention, the mixture (M) comprises from 1 to 15% by weight or from 2 to 12% by weight, of rheology modifier.

The method according to the invention advantageously uses a mixture (M) that also comprises a base. Preferably, it is an inorganic base, in particular a base chosen among NaOH, KOH, ammonium derivatives, ammonia and combinations thereof. Also preferably, it is a base chosen among the amine bases, for example triethanolamine, aminomethyl propanol or 2-amino-2-methyl-propanol (AMP) and combinations thereof.

The method according to the invention also advantageously uses a mixture (M) that has a pH of greater than 5, preferably greater than 5.5, more preferentially greater than 6. The method according to the invention also advantageously uses a mixture (M) that has a pH of less than 12.

More advantageously, the method according to the invention uses a mixture (M) that has a pH ranging from 5 to 12, preferably from 5.5 to 12, more preferentially from 6 to 12. Generally according to the invention, the mixture (M) does not comprise a surface-active compound or it has an amount of surface-active compound, preferably non-ionic, which is weak. Thus, the amount of surface-active compound, preferably non-ionic, can range from 0.05 to 10% by weight or from 0.05 to 5% by weight, of the weight of the mixture (M).

Advantageously according to the invention, the preparation temperature is lower than the boiling point of the hydrophilic phase and lower than the boiling point of the lipophilic phase. Also advantageously according to the invention, the preparation temperature is higher than the melting point of the hydrophilic phase and higher than the melting point of the lipophilic phase.

Preferably, the preparation temperature is lower than the boiling point of the hydrophilic phase and lower than the boiling point of the lipophilic phase while being higher than the melting point of the hydrophilic phase and higher than the melting point of the lipophilic phase.

The method according to the invention comprises the addition of the lipophilic compound in the continuous phase by applying a stress chosen among a shear stress and an extensional stress. Preferably, this is a shear stress.

Advantageously, the shear stress or extensional stress can be applied when preparing the mixture (M), preferably at a value equal to or less than that applied when adding the lipophilic compound.

Preferably according to the invention, the shear stress or extensional stress ranges from 300 to 5,000 Pa.

Also preferably according to the invention, the shear stress or extensional stress ranges from 100 to 2,000 Pa or from 300 to 2,000 Pa.

More preferably according to the invention, the shear stress or extensional stress ranges from 100 to 1,700 Pa or from 300 to 1,700 Pa.

According to the invention, the stress is applied using a device producing a shear gradient of less than 5,000 $s^{-1}$.

Preferably, the device used can produce a shear gradient of less than 2,000 $s^{-1}$ or less than 1,000 $s^{-1}$ Also preferably, the device used can produce a shear gradient ranging from 100 to 5,000 $s^{-1}$ or ranging from 100 to 2,000 $s^{-1}$ or ranging from 100 to 1,000 $s^{-1}$.

More preferably, the device used can produce a shear gradient ranging from 200 to 5,000 $s^{-1}$ or ranging from 200 to 2,000 $s^{-1}$ or ranging from 200 to 1,000 $s^{-1}$, in particular ranging from 200 to 800 $s^{-1}$.

Particularly advantageously, the device used is a mixer, in particular a VMI Rayneri mixer, an Ika mixer or a PC Laborsystem mixer.

The method of preparation according to the invention comprises the preparation of a continuous phase in the form of the mixture (M), then the addition of the lipophilic compound in the continuous phase by applying a shear stress. Additional steps may also be implemented in the method of preparation according to the invention.

Thus, advantageously, the method of preparation according to the invention may also comprise neutralising the dispersion (D). Preferably, neutralisation is achieved by means of at least one compound chosen among NaOH, KOH, ammonium derivatives, ammonia, amine bases, for example triethanolamine, aminomethyl propanol, or 2-amino-2-methyl-propanol (AMP) and combinations thereof.

Also advantageously, the method of preparation according to the invention may also comprise partial coacervation of the rheology-modifying compound. Preferably, partial coacervation of the rheology-modifying compound is performed by reducing the pH of the dispersion (D), for example by reducing the pH to a value of less than 6.5. The pH can be reduced by means of an acid compound, in particular by means of least one organic or inorganic acid compound, in particular an acid compound chosen among phosphoric acid, citric acid, glucono-lactone, lactic acid, salicylic acid, glycolic acid, ascorbic acid, glutamic acid, hydrochloric acid, acetic acid, D-gluconic acid, sulphonic acid,
methanesulphonic acid, benzimidazole sulphonic acid, tartaric acid, 4-aminobenzoic acid, benzoic acid, sorbic acid, phenyl benzimidazole sulphonic acid, benzylidene camphor sulphonic acid, terephthalylidene dicamphor sulphonic acid.

Also preferably, partial coacervation of the rheology-modifying compound is performed by increasing the ionic strength of the dispersion (D). Increasing the ionic strength of the dispersion (D) can be performed by adding at least one ionised compound or at least one salt, particularly NaCl, KCl, $MgCl_2$, $CaCl_2$, $MgSO_4$, $CaSO_4$.

Also preferably, partial coacervation of the rheology-modifying compound is performed by reducing the solubility of the rheology-modifying compound in the hydrophilic phase. The solubility can be reduced by adding at least one cationic polymer, particularly by adding at least one cationic polymer, in particular a cationic polymer chosen among polyquaternium 1 to polyquaternium 47 and quaternised guars, in particular guar hydroxypropyltrimonium chloride, polydiallyldimethylammonium chloride (polyDADMAC or polyDDA), poly-2-(methacryloyloxy)ethyl-trimethylammonium chloride (polyMAD quat).

The method according to the invention can combine any of these additional steps. For example, the method according to the invention may also comprise neutralising the dispersion (D) and partial coacervation of the rheology-modifying compound.

The method according to the invention makes it possible to prepare a dispersion (D) that is particularly advantageous as such. Thus, the invention also relates to a dispersion (D) that can be prepared according to the invention.

The dispersion (D) according to the invention can be used in many products which are then particularly advantageous as such. The invention therefore also relates to a product comprising at least one dispersion (D) according to the invention.

As they comprise a lipophilic phase dispersed in a continuous hydrophilic phase in the form of nanometric particles, the dispersion (D) according to the invention and the product according to the invention can be used in a great many technical fields.

Thus, the invention relates to the use of a dispersion (D) in a field chosen among cosmetics, paints, dyes, printing, inks, construction, fuels, lubricants, anti-foaming agents, metallurgy, fertilisers, pharmaceuticals, agro-chemicals, crop protection products, detergents, food, leather, coating, in particular textile coating.

The invention also relates to the use of a product according to the invention in a field chosen among cosmetics, paints, dyes, printing, inks, construction, fuels, lubricants, anti-foaming agents, metallurgy, fertilisers, pharmaceuticals, agro-chemicals, crop protection products, detergents, food, leather, coating, in particular textile coating.

The following examples illustrate the various aspects of the invention.

EXAMPLES

Example 1: Preparation of Rheology-Modifying Compounds According to the Invention 474.9 g of bi-permuted water, 6.51 g of sodium dodecyl sulphate (SDS) and 5.45 g of tridecyl alcohol tri-ethoxylate (Rhodasurf ID 030, Solvay) are introduced into a polymerisation reactor. The reactor is placed under stirring and heated to 76° C.

153 g of bi-permuted water, 2.28 g of sodium dodecyl sulphate, 0.163 g of n-dodecyl mercaptan, 109.04 g of ethyl acrylate (EA) as compound (a2), 112.5 g of methacrylic acid (MAA) as compound (a1), 45.31 g of methyl methacrylate as other compound (a2), 13.445 g of branched $C_{16}$ (25 EO) methacrylate as compound (a3) of formula (I) wherein $R^1$ represents a methacrylate group, $R^2$ represents a branched $C_{16}$-alkyl group, m=25 and n=0, 13.445 g of branched $C_{12}$ (30 EO) methacrylate as other compound (a3) of formula (I) wherein $R^1$ represents a methacrylate group, $R^2$ represents a branched $C_{12}$-alkyl group, m=30 and n=0, are weighed separately in a beaker. This mixture is placed under stirring with a magnetic bar.

A mixture containing 0.925 g of ammonium persulphate and 4.07 g of bi-permuted water and a second mixture consisting of 0.093 g of sodium bisulphite and 4.88 g of bi-permuted water are simultaneously added to the reactor. The mixture is then injected over a period of two hours. The temperature is kept at 76° C.

Polymer (P1) is obtained according to the proportions shown in Table 1 in which the values are weight ratios.

Similarly, polymers (P2), (P3), for which (a3) is a compound of formula (I) in which $R^1$ represents a methacrylate group, $R^2$ represents a tristyryl phenyl (TSP) group, m=25 and n=0, and (P4) are prepared according to the proportions (in dry g/dry weight) shown in Table 1. The total amount of monomers is 100% by weight and the amount of chain transfer agent is relative to the total amount by weight of monomers.

TABLE 1

| rheology-modifying polymer | P1 | P2 | P3 | P4 |
| --- | --- | --- | --- | --- |
| a1: MAA | 37.92 | 36.74 | 40.31 | 0.49 |
| a1: AA | / | / | / | 36.99 |
| a2: MMA | 15.58 | 27.03 | / | / |
| a2: EA | 37.50 | 27.03 | 49.73 | 53.21 |
| a3: branched $C_{12}$ (30 EO) methacrylate | 4.50 | / | / | / |
| a3: branched $C_{16}$ (25 EO) methacrylate | 4.50 | 9.21 | / | 8.21 |
| a3: TSP (25 EO) methacrylate | / | / | 8.04 | / |
| a4: AMPS | / | / | 1.92 | 1.09 |
| transfer agent: n-dodecyl mercaptan | 0.06 | 0.29 | / | / |

Example 2: Preparation of Dispersions According to the Invention

A continuous hydrophilic phase mixture (M) is prepared from rheology-modifying polymer, water and optionally from an additional hydrophilic compound and optionally from a non-ionic surface-active compound (SA) chosen among Plantaren 2000 N UP (BASF), Sensient LRT (Sensient Cosmetic Technologies), Rhodasurf ID 030 (Solvay), Polysorbate 20 (Sigma-Aldrich) and Disponil G625 (BASF).

A base is added and the mixture is placed under stirring until a homogenous aqueous mixture is obtained.

The lipophilic compound to be dispersed is prepared separately.

The lipophilic phase is then introduced, under stirring using a mixer, into the continuous hydrophilic phase to produce an emulsion.

As applicable, an acid or saline coacervation agent (acid diluent or saline diluent) is added.

Dispersions of different lipophilic compounds or mixtures of lipophilic compounds were prepared: alkyd resin 1 (viscosity 500,000 mPa·s at 70° C.), alkyd resin 2 (viscosity 6,550 mPa·s at 70° C.), alkyd resin 3 (viscosity 230 mPa·s at 70° C.), mixture of alkyd resin 1 and linoleic acid (viscosity 8,000 mPa·s at 70° C.), sunflower oil (viscosity 560 mPa·s at room temperature), n-octyltriethoxysilane (viscosity 16.7 mPa·s at room temperature).

Dispersions according to the invention are obtained according to the amounts (g) and characteristics shown in Tables 2 to 7 and for which the particle size of the dispersed lipophilic compound is less than 1 μm.

TABLE 2

| | Dispersion | D1 | D2 | D3 | D4 | D5 |
|---|---|---|---|---|---|---|
| raw materials | polymer | P1 | P2 | P2 | P2 | P3 |
| | other compound or SA | / | SDS | / | / | / |
| | base | NaOH | NaOH | NaOH | NaOH | NaOH |
| | acid | $H_3PO_4$ | $H_3PO_4$ | $H_3PO_4$ | $H_3PO_4$ | / |
| | salt | $CaCl_2$ | $CaCl_2$ | $CaCl_2$ | $CaCl_2$ | / |
| | lipophilic compound: alkyd resin | 1 | 1 | 2 | 3 | 1 |
| emulsification | mixer (at 500 s$^{-1}$) | | | VMI Rayneri | | |
| | temperature | | | 60-70° C. | | |
| continuous hydrophilic phase | dry polymer | 4.341 | 4.356 | 4.356 | 4.356 | 4.356 |
| | other dry compound or dry SA | / | 0.25 | / | / | / |
| | water | 47.699 | 45.176 | 45.176 | 45.176 | 45.176 |
| | dry base | 0.53 | 0.468 | 0.468 | 0.468 | 0.468 |
| | pH | | | 6 +/- 0.3 | | |
| | polymer (% by weight) | 8.26 | 8.67 | 8.71 | 8.71 | 8.71 |
| | stress (Pa) | 900 | 300 | 500 | 500 | 300 |
| dispersed lipophilic compound | | 77.9 | 75 | 75 | 75 | 75 |
| acid diluent | water | 29.702 | 25.152 | 25.152 | 25.152 | / |
| | acid | 0.052 | 0.048 | 0.048 | 0.048 | / |
| saline diluent | water | 14 | 14 | 14 | 14 | / |
| | salt | 0.07 | 0.07 | 0.07 | 0.07 | / |
| particle size | D50% (μm) | 0.9 | 0.8 | 0.6 | 0.5 | 0.9 |
| | D40% (μm) | 0.5 | 0.4 | 0.5 | 0.5 | 0.5 |
| | D30% (μm) | 0.4 | 0.3 | 0.5 | 0.5 | 0.4 |

TABLE 3

| | Dispersion | D6 | D7 | D8 |
|---|---|---|---|---|
| raw material | polymer | P1 | P2 | P2 |
| | other compound or SA | | Disponil G625 | |
| | base | NaOH | AMP | AMP |
| | acid | HCl | $H_3PO_4$ | D-gluconic acid |
| | salt | / | / | / |
| | lipophilic compound: alkyd resin | 1 | 1 | 1 |
| emulsification | mixer (at 500 s$^{-1}$) | VMI Rayneri | | PC Laborsystem |
| | temperature | | 60-70° C. | |
| continuous hydrophilic phase | dry polymer | 5.64 | 3.843 | 19.335 |
| | other dry compound or dry | 0.4 | 0.88 | 4.4 |
| | water | 75.06 | 30.4845 | 152.5125 |
| | dry base | 0.6 | 0.9025 | 4.5125 |
| | pH | | 6 +/- 0.3 | |
| | polymer (% by weight) | 6.90 | 10.64 | 10.70 |
| | stress (Pa) | | unavailable | |
| dispersed lipophilic compound | | 150 | 75 | 375 |
| acid diluent | water | 40.048 | 25.0272 | 190 |
| | acid | 0.092 | 0.0428 | 4.15 |
| saline diluent | water | / | 24 | / |
| | salt | / | 0.07 | / |
| particle size | D50% (μm) | 0.5 | 0.5 | 0.4 |
| | D40% (μm) | 0.4 | 0.4 | 0.3 |
| | D30% (μm) | 0.3 | 0.3 | 0.2 |

*with no alkyd resin, incremental addition

TABLE 4

| | Dispersion | D9 | D10 | D11 |
|---|---|---|---|---|
| raw material | polymer | P2 | P2 | P2 |
| | other compound or SA | Disponil G625 | Polysorbate 20 | tributyl 2-acetylcitrate |
| | base | AMP | NaOH | AMP |
| | acid | ascorbic acid | / | D-gluconic acid |
| | salt | / | NaCl | / |
| | lipophilic compound: alkyd resin | 1 | sunflower oil* | 1 |
| emulsification | mixer (at 500 s$^{-1}$) | VMI Rayneri | PC Laborsystem | VMI Rayneri |
| | temperature | 60-70° C. | room temperature | 60-70° C. |

TABLE 4-continued

|  | Dispersion | D9 | D10 | D11 |
|---|---|---|---|---|
| continuous hydrophilic phase | dry polymer | 3.93 | 22.71 | 3.7792 |
|  | other dry compound or dry SA | 0.88 | 4.1 | 0.39 |
|  | water | 30.3975 | 188.93 | 32.9008 |
|  | dry base | 0.9025 | 2.56 | 0.912 |
|  | pH | | 6 +/− 0.3 | |
|  | polymer (% by weight) | 10.88 | 10.40 | 10.00 |
|  | stress (Pa) | | unavailable | |
| dispersed lipophilic compound | | 75 | 410 | 75 |
| acid diluent | water | 38 | / | 38 |
|  | acid | 0.435 | / | 0.83 |
| saline diluent | water | 20 | 450 | / |
|  | salt | / | 3.1 | / |
| particle size | D50% (μm) | 0.5 | 0.9 | 0.9 |
|  | D40% (μm) | 0.4 | 0.8 | 0.4 |
|  | D30% (μm) | 0.3 | 0.6 | 0.3 |

*with no alkyd resin, incremental addition

TABLE 5

|  | Dispersion | D12 | D13 | D14 | D15 |
|---|---|---|---|---|---|
| raw materials | polymer | P2 | P2 | P2 | P2 |
|  | other compound or SA | / | / | Rhodasurf ID 030 | / |
|  | base | | NaOH | | |
|  | acid | | $H_3PO_4$ | | / |
|  | salt | | $CaCl_2$ | | NaCl |
|  | lipophilic compound: alkyd resin | 1 | Linoleic acid (30%) + (70%) | 1 | sunflower oil* |
| emulsification | mixer (at 500 $s^{-1}$) | PC Laborsystem | | VMI Rayneri | PC Laborsystem |
|  | temperature | | 60-70° C. | | room temperature |
| continuous hydrophilic phase | dry polymer | 21.75 | 4.356 | 4.356 | 22.71 |
|  | other dry compound or dry SA | / | / | 0.7 | / |
|  | water | 225.95 | 45.176 | 45.176 | 188.93 |
|  | dry base | 2.3 | 0.468 | 0.468 | 2.56 |
|  | pH | | 6 +/− 0.3 | | |
|  | polymer (% by weight) | 8.70 | 8.71 | 8.59 | 10.60 |
|  | stress (Pa) | 500 | 500 | 1,700 | 600 |
| dispersed lipophilic compound | | 376.2 | 75 | 75 | 434 |
| acid diluent | water | 125.26 | 25.152 | 25.152 | / |
|  | acid | 0.24 | 0.048 | 0.048 | / |
| saline diluent | water | 70 | 14 | 14 | 450 |
|  | salt | 0.35 | 0.07 | 0.07 | 3 |
| particle size | D40% (μm) | 0.8 | 0.9 | 0.9 | 0.9 |
|  | D30% (μm) | 0.5 | 0.4 | 0.4 | 0.7 |

*with no alkyd resin, incremental addition

TABLE 6

|  | Dispersion | D16 | D17 | D18 |
|---|---|---|---|---|
| raw material | polymer | P2 | P2 | P2 |
|  | other compound or SA | / | / | / |
|  | base | | NaOH | |
|  | acid | | $H_3PO_4$ | / |
|  | salt | / | $CaCl_2$ | / |
|  | lipophilic compound: alkyd resin | 1 | 1 | n-octyltriethoxysilane* |
| emulsification | mixer (at 500 $s^{-1}$) | PC Laborsystem | | VMI Rayneri |
|  | temperature | 60-70° C. | | room temperature |
| continuous hydrophilic phase | dry polymer | 21.75 | 24.06 | 2.28 |
|  | other dry compound or dry SA | / | / | / |
|  | water | 225.95 | 250.59 | 24.84 |
|  | dry base | 2.3 | 2.55 | 0.26 |
|  | pH | | 6 +/− 0.3 | |
|  | polymer (% by weight) | 8.70 | 8.68 | 8.33 |
|  | stress (Pa) | 500 | 500 | 300 |

TABLE 6-continued

| Dispersion | | D16 | D17 | D18 |
|---|---|---|---|---|
| dispersed lipophilic compound | | 377.7 | 521 | 31.8 |
| acid diluent | water | 124.76 | 244.132 | / |
| | acid | 0.24 | 0.268 | / |
| saline diluent | water | / | 70 | / |
| | salt | / | 0.42 | / |
| diluent | water | / | / | 31 |
| particle size | D30% (μm) | 0.8 | 0.9 | 0.8 |

*with no alkyd resin, incremental addition

TABLE 7

| | Dispersion | D19 | D20 | D21 |
|---|---|---|---|---|
| raw materials | polymer | P4 | P2 | P2 |
| | other compound or SA | / | Plantaren 2000 N UP | Sensient LRI |
| | base | | NaOH | |
| | acid | $H_3PO_4$ | / | / |
| | salt | $CaCl_2$ | | NaCl |
| | lipophilic compound: alkyd resin | 1 | sunflower oil* | |
| emulsification | mixer (at 500 $s^{-1}$) | | PC Laborsystem | |
| | temperature | 60-70° C. | room temperature | |
| continuous hydrophilic phase | dry polymer | 22.477 | 23.34 | 22.71 |
| | other dry compound or dry SA | / | 2 | 1.19 |
| | water | 238.943 | 187.16 | 188.93 |
| | dry base | 3.78 | 2.6 | 6.4 |
| | pH | | 6 +/− 0.3 | |
| | polymer (% by weight) | 8.48 | 10.85 | 10.54 |
| | stress (Pa) | | unavailable | |
| dispersed lipophilic compound | | 376.2 | 431.1 | 447 |
| acid diluent | water | 206.712 | / | / |
| | acid | 4.388 | / | / |
| saline diluent | water | 70 | 453.1 | 450 |
| | salt | 0.35 | 3 | 3.2 |
| particle size | D30% (μm) | 0.9 | 0.8 | 0.8 |

*with no alkyd resin, incremental addition

The method according to the invention makes it easy to prepare, using a conventional mixer producing a low shear gradient, emulsions of various lipophilic compounds dispersed in a continuous hydrophilic phase for which the size of the particles of lipophilic compound is well below 1 μm.

The invention claimed is:

1. A method of preparing a dispersion comprising a continuous hydrophilic phase and a lipophilic phase dispersed in the continuous hydrophilic phase in the form of nanometric particles, the method comprising:
    preparing a mixture comprising a hydrophilic compound and a rheology-modifying compound of the hydrophilic compound, and
    adding a lipophilic compound in the continuous hydrophilic phase by applying, using a device producing a shear gradient of less than 5,000 $s^{-1}$, a stress chosen among a shear stress ranging from 100 to 5,000 Pa and an extensional stress ranging from 100 to 5,000 Pa,
    wherein the continuous hydrophilic phase comprises the hydrophilic compound and the rheology-modifying compound, and
    the rheology-modifying compound is an anionic copolymer.

2. The method according to claim 1, wherein:
    the continuous hydrophilic phase has a viscosity ranging from 20 to 50,000 mPa·s;
    the dispersion has a viscosity ranging from 20 to 50,000 mPa·s;
    the dispersion is an emulsion; or
    the dispersion comprises from 0.1 to 75% by weight of dispersed lipophilic phase relative to the total amount by weight of the continuous hydrophilic phase and of the dispersed lipophilic phase.

3. The method according to claim 1, wherein the hydrophilic compound is chosen among water alone or in combination with at least one compound chosen among glycerol, polyglycerols, glycols, moistening compounds, sugar derivatives, and coalescing agents.

4. The method according to claim 1,
    wherein the rheology-modifying compound has a pH greater than 5; or
    the rheology-modifying compound is at least one selected from the group consisting of an ASE copolymer and a HASE copolymer.

5. The method according to claim 1, wherein the mixture also comprises a base; and
the mixture has a pH greater than 5.

6. The method according to claim 1, wherein the mixture comprises from 0.5 to 15% by weight of a rheology modifier.

7. The method according to claim 1, wherein:
the preparation temperature is lower than a boiling point of the continuous hydrophilic phase and lower than a boiling point of the lipophilic phase;
the preparation temperature is higher than a melting point of the continuous hydrophilic phase and higher than a melting point of the lipophilic phase; or
the preparation temperature is lower than the boiling point of the continuous hydrophilic phase and lower than the boiling point of the lipophilic phase while being higher than the melting point of the continuous hydrophilic phase and higher than the melting point of the lipophilic phase.

8. The method according to claim 1, wherein the dispersion is an emulsion of a dispersed lipophilic phase in the continuous hydrophilic phase.

9. The method according to claim 1, wherein the shear stress or the extensional stress ranges from 300 to 5,000 Pa;
the shear stress or the extensional stress is also applied when preparing the mixture; or
the stress is applied using a device that produces a shear gradient of less than 2,000 s$^{-1}$ or using a device that produces a shear gradient ranging from 100 to 5,000 s$^{-1}$.

10. The method according to claim 1,
wherein a mean size (measured by light scattering) of dispersed particles of lipophilic phase is submicronic.

11. The method according to claim 1, further comprising:
neutralisation of the dispersion; or
partial coacervation of the rheology-modifying compound.

12. A dispersion prepared by the method according to claim 1.

13. A product comprising the dispersion according to claim 12.

14. An article, comprising the dispersion according to claim 12 wherein the article is selected from the group consisting of cosmetics, paints, dyes, printing, inks, construction, fuels, lubricants, anti-foaming agents, metallurgy, fertilisers, pharmaceuticals, agro-chemicals, crop protection products, detergents, food, leather, and coating.

15. The method according to claim 5, wherein the pH ranges from greater than 5 to 12.

16. The method according to claim 1, wherein the mixture further comprises from 0.05 to 10% by weight of the mixture of a surface-active compound.

17. The method according to claim 1, wherein the mixture does not comprise any surface-active compound.

* * * * *